United States Patent
Baek

(10) Patent No.: US 11,938,340 B2
(45) Date of Patent: Mar. 26, 2024

(54) MERIDIAN STIMULATION DEVICE

(71) Applicant: Sung Wook Baek, Seoul (KR)

(72) Inventor: Sung Wook Baek, Seoul (KR)

( * ) Notice: Subject to any disclaimer, the term of this patent is extended or adjusted under 35 U.S.C. 154(b) by 0 days.

(21) Appl. No.: 17/918,891

(22) PCT Filed: Mar. 12, 2021

(86) PCT No.: PCT/KR2021/003092
§ 371 (c)(1),
(2) Date: Sep. 20, 2023

(87) PCT Pub. No.: WO2021/210789
PCT Pub. Date: Oct. 21, 2021

(65) Prior Publication Data
US 2024/0033537 A1 Feb. 1, 2024

(30) Foreign Application Priority Data
Apr. 14, 2020 (KR) .................... 10-2020-0045414

(51) Int. Cl.
*A61N 5/06* (2006.01)

(52) U.S. Cl.
CPC .... *A61N 5/0619* (2013.01); *A61N 2005/0626* (2013.01); *A61N 2005/0651* (2013.01); *A61N 2005/0663* (2013.01); *A61N 2005/0667* (2013.01)

(58) Field of Classification Search
CPC .......... A61N 5/0619; A61N 2005/0626; A61N 2005/0651; A61N 2005/0663; A61N 2005/0667
See application file for complete search history.

(56) References Cited

U.S. PATENT DOCUMENTS

| 2005/0004631 A1 | 1/2005 | Benedict |
| 2007/0268604 A1* | 11/2007 | Sasaki .................. A61N 5/0616 359/891 |
| 2008/0139976 A1 | 6/2008 | Sugiyama et al. |

(Continued)

FOREIGN PATENT DOCUMENTS

| JP | H11-508150 A | 7/1999 |
| JP | 2005-027702 A | 2/2005 |
| JP | 2007307724 A | 11/2007 |

(Continued)

OTHER PUBLICATIONS

Litscher, "Infrared thermography fails to visualize stimulation-induced meridian-like structures", BioMedical Engineering OnLine. BioMed Central, 2005, pp. 1-8.

(Continued)

*Primary Examiner* — Tammie K Marlen
*Assistant Examiner* — Aya Ziad Bakkar
(74) *Attorney, Agent, or Firm* — Seed IP Law Group LLP

(57) ABSTRACT

A meridian stimulation device according to the present specification may comprise: a power supply unit that supplies power; a detection unit that detects the cardiac cycle of a user while attached to the skin of the user; at least one pad attached to a predetermined position on the user and including a light emitting unit that emits visible light, and a filter through which the visible light is transmitted; and a control unit that controls the operation of the light emitting unit on the basis of the cardiac cycle of the user.

6 Claims, 12 Drawing Sheets

(56) References Cited

U.S. PATENT DOCUMENTS

2016/0375264 A1* 12/2016 Laperriere .......... A61N 5/0603
                                                          433/29
2022/0059717 A1   2/2022 Lin et al.

FOREIGN PATENT DOCUMENTS

| JP | 2009142543 A |   | 7/2009 |
| KR | 10-2008-0030520 A |   | 4/2008 |
| KR | 2008094640 A | * | 10/2008 |
| KR | 10-1025473 B1 |   | 4/2011 |
| KR | 10-1258210 B1 |   | 4/2013 |
| KR | 10-1326540 B1 |   | 11/2013 |
| KR | 10-2013-0131584 A |   | 12/2013 |
| KR | 10-1385712 B1 |   | 4/2014 |
| KR | 10-2020-0031830 A |   | 3/2020 |
| KR | 10-2192665 B1 |   | 12/2020 |
| TW | 200628188 A |   | 8/2006 |
| TW | 202021150 A |   | 6/2020 |

OTHER PUBLICATIONS

Ling et al, "Infrared thermography and meridian-effect evidence and explanation in Bell's palsy patients treated by moxibustion at the Hegu (LI4) acupoint", Neural Regeneration Research, vol. 7, Issue 9, pp. 680-685, Mar. 2012.

* cited by examiner

< Continuous emission of visible light >

< Visible light emission Hz=1.8 >

< Visible light emission Hz=1.2 >

MERIDIAN STIMULATION DEVICE

BACKGROUND

Technical Field

An example embodiment of the present specification relates to a meridian stimulation device, and specifically, to a meridian stimulation device in which visible light emitted based on a heartbeat cycle passes through a filter composed of a mixture of a plurality of minerals to stimulate specific acupuncture point on the meridians.

Description of the Related Art

In general, acupuncture is widely used as a means of treatment in oriental medicine. At this time, the theoretical basis of oriental medicine is based on meridians. In oriental medicine, meridians connect multiple acupuncture point, and may be a passageway through which energy, which is Qi, flows. At this time, the acupuncture point is a position with a special function on the meridian as a passageway through which the meridian communicates with the outside, and may be a position where the flow of qi inside the body is controlled through acupuncture. For example, in oriental medicine, it is believed that diseases may be cured by stimulating the acupuncture point through acupuncture and facilitating the flow of energy flowing through the meridians.

However, it is also true that there are criticisms of oriental medicine as unscientific medical practice because the substance of meridians and acupuncture point has not yet been clearly identified. Accordingly, there have been various studies to identify the substance of meridians and acupuncture point.

BRIEF SUMMARY

The inventors have realized that while there have been some achievements regarding identifying the substance of meridians and acupuncture point, the substance of meridians and acupuncture point discovered through various studies was not objective, not reproducible, and there were problems that were inconsistent with the classical meridian diagram of oriental medicine.

One or more embodiments of the present specification addresses the various technical problems in the related art including the problem identified above. One or more embodiments provide a technique related to a meridian stimulation device in which visible light emitted based on a heartbeat cycle passes through a filter composed of a mixture of a plurality of minerals to stimulate specific acupuncture point on the meridians. At this time, the visible light emitted based on the heartbeat cycle passes through the filter and stimulates the acupuncture point, thereby increasing the temperature along the meridians, whereby the substance of the meridians may be identified. Therefore, the substance of the meridians may be objectively identified through the visualization of the meridians by the meridian stimulation device. The technical matters to be solved by the present example embodiment are not limited to the technical matters described above, and other technical matters may be inferred from the following example embodiments.

In order to solve the above matters, the meridian stimulation device according to an example embodiment of the present specification may include a power supply unit for supplying power; a detection unit which detects the user's heartbeat cycle while being attached to the user's skin; at least one pad comprising a light emitting unit emitting visible light and a filter through which the visible light is transmitted, the pad being attached to a predetermined position for the user; and a controller for controlling an operation of the light emitting unit based on the heartbeat cycle of the user.

According to an example embodiment, the controller may control the light emitting unit to periodically emit the visible light in consideration of the heartbeat cycle of the user.

According to an example embodiment, the filter may include at least one of iron (Fe), magnesium (Mg), calcium (Ca), lithium (Li), zinc (Zn), copper (Cu), molybdenum (Mo), chromium (Cr), nickel (Ni) and nobelium (No), and selenium (Se).

According to an example embodiment, in the filter, at least one of the iron (Fe), the magnesium (Mg), the calcium (Ca), the lithium (Li), the zinc (Zn), the copper (Cu), and the molybdenum (Mo), the chromium (Cr), the nickel (Ni) and the nobelium (No), and the selenium (Se) may be configured in different ratios corresponding to the preset positions.

According to an example embodiment, the predetermined position may be a position corresponding to the user's acupuncture point and may be stimulated by the visible light passing through the filter.

According to an example embodiment, the at least one pad may include a filter composed of elements having different ratios corresponding to different predetermined positions of the user.

According to an example embodiment, the controller may control the intensity of the emitted visible light in consideration of a predetermined position of the user.

According to an example embodiment, the meridian stimulation device further comprises a communication unit for receiving the learned data from an external server, wherein the controller reflects the learned data to control the operation of the light emitting unit.

Specific details of other example embodiments are included in the detailed description and drawings.

According to an example embodiment of the present specification, there are one or more of the following technical benefits.

First, the visible light emitted based on the heartbeat cycle passes through a filter composed of a mixture of a plurality of minerals and stimulates specific acupuncture point on the meridians, thereby increasing the temperature along the meridians, the substance of the meridians may be confirmed.

Second, by using a non-invasive method using light, it is possible to reduce or eliminate the occurrence of infection at the treatment site and to treat the disease without pain. In addition, since it is reusable, the cost of waste disposal may be reduced.

Third, due to the miniaturization and weight reduction of the meridian stimulation device, it is easy to carry and may be fixed to the user's body, so that the user may perform treatment using the meridian stimulation device while performing daily life.

Technical benefits of the disclosure are not limited to the effects mentioned above, and other effects not mentioned will be clearly understood by those skilled in the art from the description of the claims.

DETAILED DESCRIPTION

Figure 1:
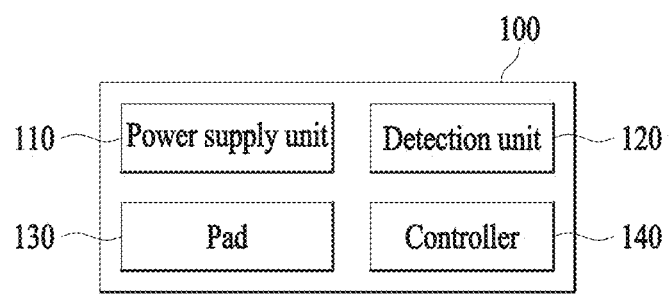
FIG. 1 is a diagram illustrating a block diagram of a meridian stimulation apparatus according to an example embodiment.

Hereinafter, the embodiments disclosed in the present specification will be described in detail with reference to the accompanying drawings, but the same or similar components are assigned the same reference numerals regardless of reference numerals, and redundant description thereof will be omitted. The suffixes "module" and "part" for the components used in the following description are given or mixed in consideration of only the ease of writing the specification, and do not have distinct meanings or roles by themselves. In addition, in describing the embodiments disclosed in the present specification, if it is determined that detailed descriptions of related known technologies may obscure the gist of the embodiments disclosed in the present specification, the detailed description thereof will be omitted. In addition, the accompanying drawings are only for easy understanding of the embodiments disclosed in the present specification, and the technical spirit disclosed in the present specification is not limited by the accompanying drawings, and it should be understood to include all modifications, equivalents and substitutes included in the spirit and scope of the present disclosure.

Terms including an ordinal number, such as first, second, and the like, may be used to describe various components, but the components are not limited by the terms. The above terms are used only for the purpose of distinguishing one component from another.

When a component is referred to as being "connected" or "accessed" to another component, it may be directly connected or accessed to the other component, but it should be understood that other components may exist in between. On the other hand, when it is said that a certain component is "directly connected" or "directly accessed" to another component, it should be understood that the other component does not exist in between.

The singular expression includes the plural expression unless the context clearly dictates otherwise.

In the present application, terms such as "comprises" or "have" are intended to designate that a feature, number, step, operation, component, part, or combination thereof described in the specification exists, but it should be understood that this does not preclude the possibility of addition or existence of one or more other features or numbers, steps, operations, components, parts, or combinations thereof.

The term "unit" as used throughout herein may include any electrical circuitry, features, components, an assembly of electronic components or the like. That is, "unit" may include any processor-based or microprocessor-based system including systems using microcontrollers, integrated circuit, chip, microchip, reduced instruction set computers (RISC), application specific integrated circuits (ASICs), field-programmable gate arrays (FPGAs), graphical processing units (GPUs), logic circuits, and any other circuit or processor capable of executing the various operations and functions described herein. The above examples are examples only, and are thus not intended to limit in any way the definition or meaning of the term "unit."

In some embodiments, the various units described herein may be included in or otherwise implemented by processing circuitry such as a microprocessor, microcontroller, or the like.

In describing the example embodiments, descriptions of technical contents that are well known in the technical field to which the present disclosure pertains and are not directly related to the present disclosure will be omitted. This is to more clearly convey the gist of the present disclosure without obscuring the gist of the present disclosure by omitting unnecessary description.

For the same reason, some components are exaggerated, omitted, or schematically illustrated in the accompanying drawings. In addition, the size of each component does not fully reflect the actual size. In each figure, the same or corresponding elements are assigned the same reference numerals.

Advantages and features of the present disclosure, and a method for achieving them will become apparent with reference to the embodiments described below in detail in conjunction with the accompanying drawings. However, the present disclosure is not limited to the embodiments disclosed below, but may be implemented in various different forms, and only the present embodiments allow the disclosure of the present disclosure to be complete, and it is provided to fully inform those of ordinary skill in the art to which the present disclosure pertains. Like reference numerals refer to like elements throughout.

FIG. 1 is a diagram illustrating a block diagram of a meridian stimulation device according to an example embodiment.

Referring to FIG. 1, the meridian stimulation device 100 may include at least one of a power supply circuit 110 (also referred to as "a power supply unit 110), a detection circuit 120 (also referred to as "a detection unit 120), a pad 130, and a controller 140. The power supply unit 110 may supply power to the meridian stimulation device 100, and the detection unit 120 may detect the user's heartbeat cycle while being attached to the user's skin. The detection unit 120 may monitor the user's heartbeat cycle and detect a change in the heartbeat cycle according to the user's movement. As a method for the detection unit 120 to detect and monitor a heartbeat cycle, a method generally used in the related art may be applied.

In addition, the pad 130 may include a light emitting unit emitting visible light and a filter through which visible light is transmitted, and the pad 130 may be attached to a predetermined position for the user. Specifically, the light emitting unit may emit light in a visible ray region, for example, the light emitting unit may emit light in a wavelength region of 380 to 770 nanometer (nm). Visible light emitted from the light emitting unit may pass through the filter to reach the user's predetermined position. In this case, the user's predetermined position is a position corresponding to acupuncture point, and may be stimulated by visible light passing through the filter. In this case, the light emitting unit is a light source emitting light in the visible ray region, and may be, for example, a Light Emitting Diode (LED). Since the LED has a narrow wavelength bandwidth and emits a light source of a specific wavelength, it may not emit harmful ultraviolet rays or unnecessary infrared rays.

In this case, the filter may be formed by mixing a plurality of minerals. For example, the filter may be formed by mixing at least one of 30 kinds of minerals such as iron (Fe), magnesium (Mg), calcium (Ca), lithium (Li), zinc (Zn), copper (Cu), molybdenum (Mo), chromium (Cr), nickel (Ni) and Nobelium (No), and selenium (Se). In this case, selenium has an effect of activating the human body, such as anti-aging due to its antioxidant effect, inhibiting cancer occurrence, urogenital treatment, and strengthening immunity.

Specifically, the filter may be configured in different ratios corresponding to predetermined positions of at least one of 30 kinds of minerals such as iron (Fe), magnesium (Mg), calcium (Ca), lithium (Li), zinc (Zn), copper (Cu), molybdenum (Mo), chromium (Cr), nickel (Ni) and Nobelium (No), and selenium (Se). In order to treat a disease by stimulating a predetermined position by the visible light passing through the filter, the filter may be configured at a different ratio for each predetermined position. For example, to treat chronic kidney disease (CKD) by stimulating an acupuncture point located in the Spleen Meridian or Kidney Meridian, the filter may be made by mixing multiple minerals and selenium in a ratio of 32:1. Chronic kidney disease (CKD) may be treated without using any drugs, and by stimulating acupuncture point with visible light passing through a filter formulated in a specific ratio.

In this case, the filter may be located in a path through which visible light is emitted in various shapes. For example, the filter may be attached to one surface of the light emitting unit in the form of a film, and visible light emitted from the light emitting unit may pass through the filter in the form of a film.

In this case, the pad may include filters composed of elements having different ratios corresponding to different predetermined positions of the user. Specifically, a filter used to stimulate different acupuncture point to treat different diseases may be made by mixing a plurality of minerals and selenium in different ratios.

Acupuncture point located in meridians has a natural frequency, and if the acupuncture point are stimulated with the same frequency as the natural frequency, the temperature may rise along the meridians due to resonance. Specifically, when the acupuncture point located in the meridians is stimulated using visible light emitted based on the heartbeat cycle, the temperature may increase along the meridians due to resonance. Accordingly, the controller 140 may control the operation of the light emitting unit based on the user's heartbeat cycle. When the detection unit 120 detects the user's heartbeat cycle, the controller 140 may control the operation of the light emitting unit in consideration of the heartbeat cycle. Even if the heartbeat cycle changes according to the user's movement, the detection unit 120 may detect the changed heartbeat cycle, and the controller 140 may control the operation of the light emitting unit in consideration of the changed heartbeat cycle. Specifically, the controller 140 may control the operation of the light emitting unit so that the blinking cycle of visible light corresponds to the heartbeat cycle n:1 (where n is an integer). For example, the controller 140 may control the operation of the light emitting unit so that the blinking cycle of visible light and the heartbeat cycle correspond to 1:1. Therefore, the visible light may stimulate the acupuncture point at every moment of beating at the location of the acupuncture point. As another example, the controller 140 may control the operation of the light emitting unit so that the blinking cycle of visible light and the heartbeat cycle correspond to 2:1. Therefore, the visible light may stimulate the acupuncture point every time the pulse is twice at the location of the acupuncture point. As another example, when the pad 130 is attached to a plurality of positions similar to placing acupuncture on various sites in oriental medicine, the blinking cycle of visible light emitted through each pad 130 may be different.

Also, the controller 140 may control the wavelength of visible light emitted from the light emitting unit in consideration of the user's predetermined position. Specifically, in order to obtain a therapeutic effect by stimulating a predetermined position using a meridian stimulation device, the controller may control the wavelength of visible light emitted from the light emitting unit. A predetermined position of the user stimulated by the meridian stimulation device may be different depending on the treatment purpose, and the controller may control the wavelength of visible light emitted from the light emitting unit in consideration of the predetermined position. For example, light having a wavelength of 310 to 330 nm may be suitable for treating atopic dermatitis, light having a wavelength of 410 to 430 nm may be suitable for treating acne, and light having a wavelength of 630 to 660 nm may be suitable for skin whitening and skin aging prevention. Accordingly, the controller may control the light emitting unit to emit light of a wavelength of 630 to 660 nm in the visible ray region in order to stimulate the user's predetermined position for skin whitening and skin aging prevention purposes, or the controller may control the light emitting unit to emit light having a wavelength of 410 to 430 nm in the visible ray region in order to stimulate a predetermined position of the user for the purpose of treating atopic dermatitis.

Also, as in oriental medicine using long and short needles of different lengths, the meridian stimulation device may control the degree to which acupuncture point is stimulated by using the intensity of emitted visible light. The controller 140 may control the intensity of visible light emitted from the light emitting unit in consideration of the user's predetermined position. For example, when stimulating an acupuncture point located in the Spleen Meridian and when stimulating an acupuncture point located in the Pericardium Meridian, the controller 140 may differently control the intensity of visible light emitted from the light emitting unit. Here, the Pericardium Meridian is a meridian related to heart disease, fatigue recovery, rheumatism, paralysis of the hand, and the like, and includes 9 acupuncture points.

At this time, if the intensity of visible light emitted from the light emitting unit is weak, the meridian stimulation effect may be weak, and if the intensity is strong, the skin may be irritated or the battery may be consumed quickly. Accordingly, the light emitting unit may emit visible light with an appropriate intensity. For example, the meridian stimulation device may stimulate the acupuncture point using visible light in the range of 300 to 1000 lux. Specifically, the meridian stimulation device may stimulate the acupuncture point using 800 lux visible light.

In addition, the meridian stimulation device may further include a display unit (not shown). The display unit may display whether a position to which the pad 130 is attached corresponds to acupuncture point. The meridian stimulation device may determine whether a position to which the pad 130 is attached corresponds to acupuncture point using a method generally used in the related art. When the position to which the pad 130 is attached does not correspond to acupuncture point, the meridian stimulation device may display an indication indicating adjustment of the position to which the pad 130 is attached through the display unit. Therefore, even if non-specialists use the meridian stimulation device, the meridians may be stimulated by attaching the pad 130 to the correct position corresponding to the acupuncture point. For example, the meridian stimulation device may supply a current to the user's body through the pad 130 and measure the impedance value using the voltage generated in the user's body. The meridian stimulation device may determine whether the position to which the pad 130 is attached corresponds to the acupuncture point by comparing the reactance extracted from the impedance with the reference reactance. Here, the reference reactance is a reactance value corresponding to the corresponding acupuncture point, and may be a statistical value determined through an experiment in advance. If it does not correspond to acupuncture point, the meridian stimulation device may instruct adjustment of the position to which the pad 130 is attached through the display unit.

According to an example embodiment, the acupuncture point located in the meridians have a natural frequency, and when the corresponding acupuncture point is stimulated with the same frequency as the natural frequency, the temperature may increase along the meridians due to resonance. Specifically, when acupuncture points located in the meridians are stimulated using visible light emitted based on the heartbeat cycle, the meridian-pulsing ion current is generated due to resonance, and the temperature increase along the meridians as a result of the electrochemical reactions occurring along the pulsating ion current path may be confirmed through the thermal imaging camera. At this time, since the blood vessels or lymphatic vessels of the human body cannot have such a temperature increase physiologically, it may be seen that energy flows along the meridians. Diseases may be cured by such a flow of energy. Here, by connecting the parts where the temperature increases, it may be confirmed that it is similar to the meridians on the classical meridian diagram, and the objective substance of the meridians may be identified through the visualization of the meridians by the temperature increase. For example, by stimulating acupuncture points located in the Kidney Meridian, energy flows along the Kidney Meridian to improve kidney function, thereby treating chronic kidney disease (CKD). When acupuncture points were stimulated using a meridian stimulation device for 50 to 60 minutes a day for chronic kidney disease (CKD) patients (31 males, 18 females), it was confirmed actually that the patients' creatine levels improved from 3.6±0.5 mg/dl to 0.8±0.2 mg/dl after 1 to 2 months.

Here, the Kidney Meridian is a meridian related to kidney disease, lower extremity paralysis, drug addiction, sore throat, diabetes, respiratory disease, gynecological disease, cold, asthma, and the like, and includes 27 acupuncture points. When acupuncture points located in the Kidney Meridian are stimulated using the meridian stimulation device, it can be confirmed through the thermal imaging camera that the body temperature increases along the Kidney Meridian.

Figure 2:
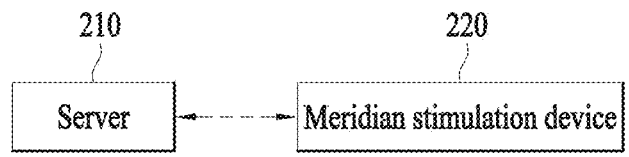
FIG. 2 is a diagram illustrating a server and a meridian stimulation apparatus according to an example embodiment.

FIG. 2 is a diagram illustrating a server and a meridian stimulation apparatus according to an example embodiment.

Referring to FIG. 2, the server 210 may communicate with the meridian stimulation device 220. The server 210 and the meridian stimulation device 220 may include a communication circuit (or also referred to as "a communication unit") capable of transmitting and receiving data using wired/wireless communication. The above description is applicable here. In this case, the communication technology used by the communication unit may include Global System for Mobile communication (GSM), Code Division Multi Access (CDMA), Long Term Evolution (LTE), 5G, Wireless LAN (WLAN), Wireless-Fidelity (Wi-Fi), Bluetooth (Bluetooth™), Radio Frequency Identification (RFID), Infrared Data Association (IrDA), ZigBee, Near Field Communication (NFC), and the like.

The server 210 may learn by receiving the relevant data from the meridian stimulation device 220, and may update the existing data. Specifically, the server 210 may receive a treatment effect according to the user's characteristics (for example, age, height, weight, exercise habit, eating habits, and the like) from the meridian stimulation device 220. The server 210 that has received the related data may manage the related data by applying a neural network to analyze and learn the related data. For example, the server 210 may analyze and learn the treatment effect according to the age and manage it, or may analyze and learn the treatment effect according to the height and weight and manage it, or may analyze and learn the treatment effect according to the exercise habits and eating habits and manage it.

The meridian stimulation device 220 may receive the learned data from the server 210, and the controller may control the operation of the light emitting unit by reflecting the learned data. For example, the controller may control the operation of the light emitting unit in consideration of the data received from the server 210 and the heartbeat cycle of the user.

In addition, the meridian stimulation device 220 may continuously detect data related to the user and transmit it to the server 210, and the server 210 may monitor the health status of the user using the accumulated data related to the user. In addition, the meridian stimulation device 220 reflects the accumulated data so that personalized medical services may be provided to the individual by stimulating the acupuncture point. The meridian stimulation device 220 transmits the result of regular or irregular execution to the server 210, and the server 210 may monitor the user's health condition using the related data. The server 210 transmits related information to the meridian stimulation device 220 so that acupuncture points may be stimulated for the purpose of treatment or prevention when a disease has occurred or a disease is expected, and the meridian stimulation device 220 may treat or prevent disease by stimulating the user's meridians by reflecting the relevant information.

Figure 3:
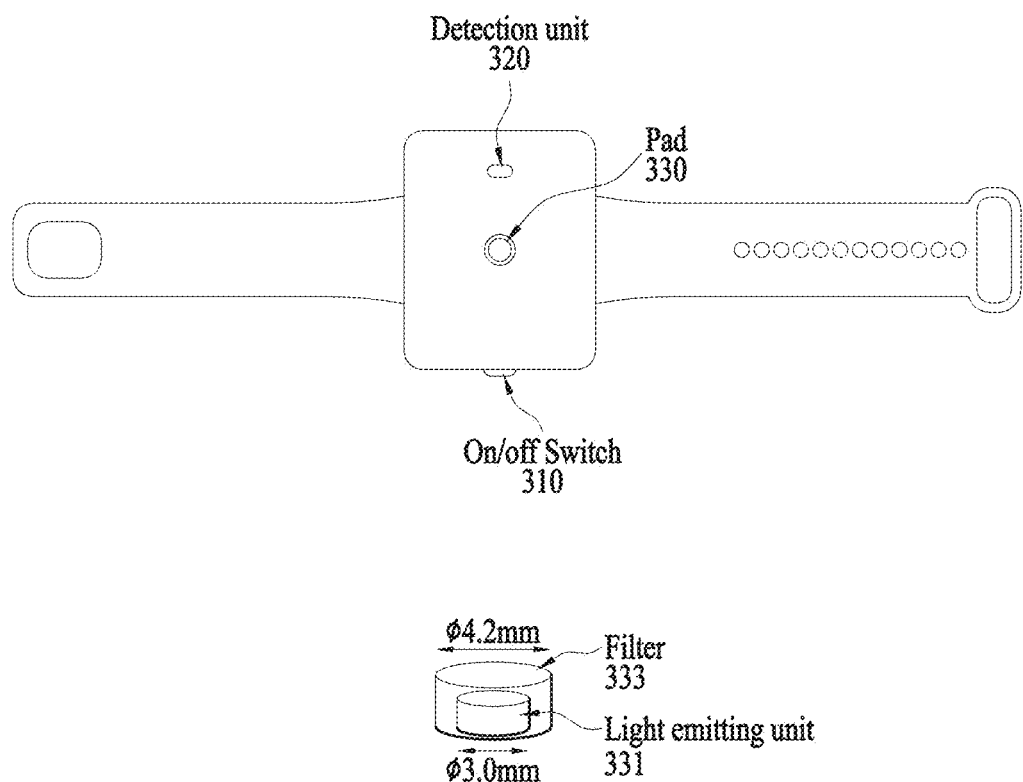
FIG. 3 is a diagram illustrating a meridian stimulation device in the form of a wearable device according to an example embodiment.

FIG. 3 is a diagram illustrating a meridian stimulation device in the form of a wearable device according to an example embodiment.

Referring to FIG. 3, the meridian stimulation device may be a wearable device worn on the user's body in the form of a watch. The above description is applicable here. A wearable device may be a device worn on a user's body. For example, the wearable device may be worn on the user's body in various forms such as a ring, a watch, glasses, a bracelet, a belt, a band, a necklace, an earring, a helmet, or clothes.

The meridian stimulation device may include an on/off switch 310. By manipulating the on/off switch 310, power may or may not be supplied from the power supply unit.

In addition, the meridian stimulation device may include a detection unit 320. The detection unit 320 may monitor the user's heartbeat cycle and detect a change in the heartbeat cycle according to the user's movement.

In addition, the meridian stimulation device may include a pad (330). The pad 330 may include a filter 333 and a light emitting unit 331. The pad 330 of the meridian stimulation device as shown in FIG. 3 includes one filter 333 and one light emitting unit 331, and the scope of the present disclosure is not limited thereto and may include a variable number of pads 330 as shown in FIG. 4.

The pad 330 of the meridian stimulation device may have a cylindrical shape with a diameter of 4.2 mm, the light emitting unit 331 may have a cylindrical shape with a diameter of 3.0 mm, and the filter 333 may be attached to one surface of the light emitting unit 331. For example, the filter 333 may be attached to one surface of the light emitting unit 331 in the form of a film. Such a shape and size are merely examples, and the scope of the present disclosure is not limited thereto.

Figure 4:
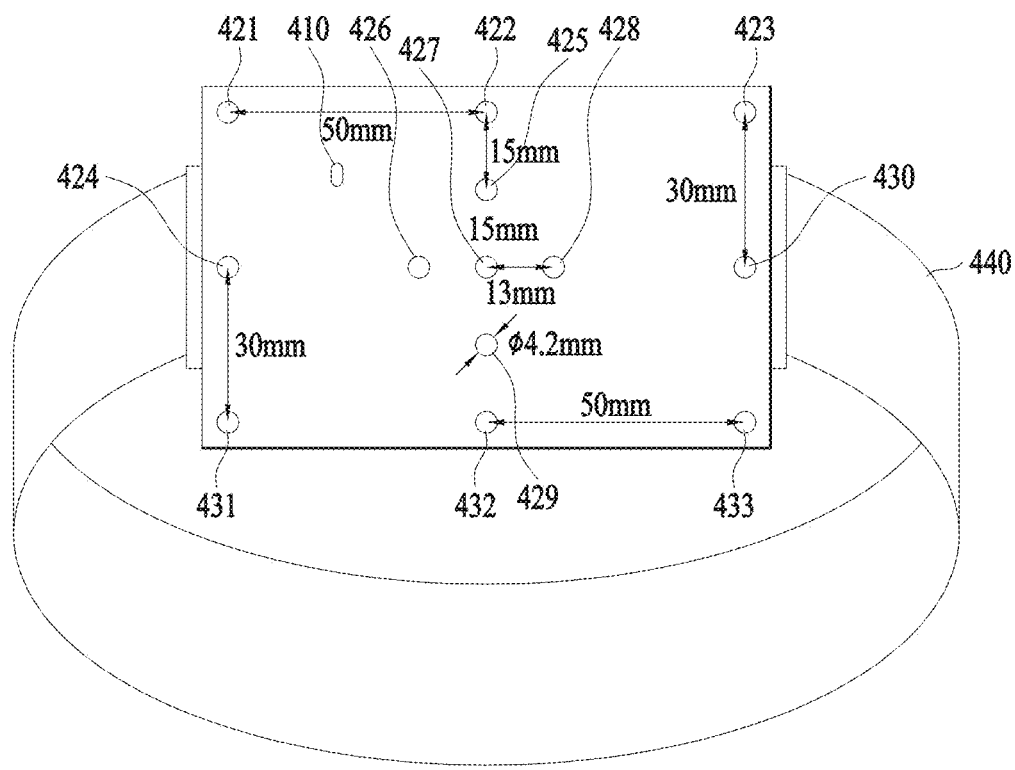
FIG. 4 is a diagram illustrating a meridian stimulation device according to another example embodiment.

FIG. 4 is a diagram illustrating a meridian stimulation device according to another example embodiment.

The meridian stimulation device may include one detection unit 410 and a plurality of pads. Similar to placing acupuncture on multiple acupuncture points to increase the therapeutic effect in oriental medicine, unlike FIG. 3, the meridian stimulation device may stimulate multiple acupuncture points using a plurality of pads. The above description is applicable here.

In this case, a meridian stimulation device having a different number of pads corresponding to the portion to be attached to the user may be used. For example, as shown in FIG. 4, the meridian stimulation device may include 13 pads 421 to 433. In addition, a meridian stimulation device having a different size corresponding to the user's part may be used. For example, the meridian stimulation device of FIG. 4 has a size of 110 mm*70 mm, but when applied to other parts, a meridian stimulation device of a different size may be used.

As described above, the detection unit 410 may detect the heartbeat cycle of the user. The detection unit 410 may be located on the same plane as the pad as shown in FIG. 4 or may exist separately.

As an example, as shown in FIG. 4, the pad may include a pad 421, a pad 422, a pad 423, a pad 424, a pad 425, a pad 426, a pad 427, a pad 428, a pad 429, a pad 430, a pad 431, a pad 432, and a pad 433. At this time, the meridian stimulation device may stimulate the acupuncture points through visible light emitted from each of the pads 421 to 433.

In this case, the arrangement relationship of the 13 pads may be different according to the user's part. For example, even if 13 pads are used, the arrangement relationship of the pads may be different when used on the user's abdomen and when used on the user's waist.

In addition, as shown in FIG. 4, between the pad 421 and the pad 422 and between the pad 432 and the pad 433 may be spaced 50 mm apart, and between the pad 421 and the pad 424 and between the pad 424 and the pad 431 may be spaced apart by 30 mm, between the pad 425 and the pad 427 and between the pad 422 and the pad 425 may be spaced apart by 15 mm, and between the pad 427 and the pad 428 may be spaced apart by 13 mm. The separation distance of the 13 pads is merely an example, and the separation distance may be different according to the user's part.

The meridian stimulation device may stimulate the acupuncture points using visible light emitted from each pad 421 to 433 based on the heartbeat cycle. The controller included in the meridian stimulation device may generate a driving signal to control the operation of the light emitting unit. Details of the driving signal will be described in FIG. 6 below.

The controller may transmit a driving signal to the light emitting unit, and the light emitting unit may control an operation according to the driving signal. In this case, each pad may receive different driving signals. Specifically, the controller may transmit a driving signal to the light emitting unit to emit visible light in a specific order by applying the delay time calculated for each pad. Accordingly, similar to the order of placing needles on the body part, the order of the pads emitting visible light may be controlled by the driving signal. For example, when the pad 427 emits visible light based on the heartbeat cycle by each driving signal, the pads 425, 426, 428, and 429 may emit visible light with a delay of 1 period, and the pads 421, 422, 423, 424, 430, 431, 432, and 433 may emit visible light with a delay of 2 cycles.

Also, the controller may transmit a driving signal to the light emitting unit to emit visible light at a specific period by applying a period calculated for each pad. For example, when the pad 427 emits visible light at a cycle corresponding to 1:1 with the heartbeat cycle by each driving signal, the pads 425, 426, 428, and 429 may emit visible light at a period corresponding to 2:1 with a heartbeat cycle, and the pads 421, 422, 423, 424, 430, 431, 432, and 433 may emit visible light at a period corresponding to 4:1 with a heartbeat cycle.

In addition, the meridian stimulation device may include a band 440, and even if the user does not hold the meridian stimulation device by hand, the meridian stimulation device may be fixed to the user's body by the band 440.

Figure 5:
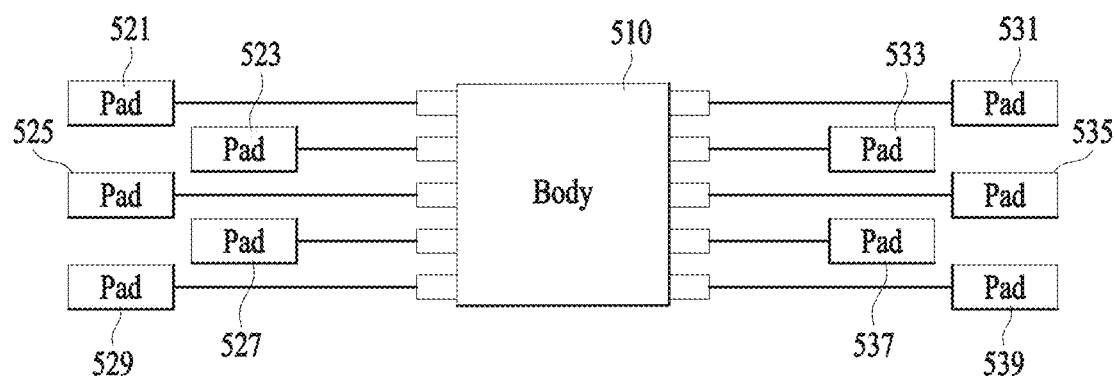
FIG. 5 is a diagram illustrating a meridian stimulation device according to still another example embodiment.

FIG. 5 is a diagram illustrating a meridian stimulation device according to still another example embodiment.

The pad may be built into the body as shown in FIG. 3 and FIG. 4, or the pads 521 to 539 may not be built into the body 510 as shown in FIG. 5. The meridian stimulation device may include a body 510 and at least one pad 521 to 539. In this case, the body 510 may include a power supply unit for supplying power, and a controller for controlling the operation of the light emitting unit based on the user's heartbeat cycle. The detection unit may be built into the body 510 or may transmit/receive data related to the body 510 through wired or wireless. The pads 521 to 539 are merely an example, and the scope of the present disclosure may include a case in which the number of pads is different.

The pads 521 to 539 may include filters composed of elements having different ratios corresponding to different predetermined positions of the user. In order to improve the therapeutic effect, the pads 521 to 539 may include filters composed of elements in different ratios. That is, a filter used to stimulate different acupuncture points to treat different diseases may be made by mixing a plurality of minerals and selenium in different ratios. For example, the pad 521 attached to the acupuncture point located in the Spleen Meridian and the pad 523 attached to the acupuncture point located in the Pericardium Meridian may include a filter configured by mixing a plurality of minerals and selenium in different ratios.

Figure 6:
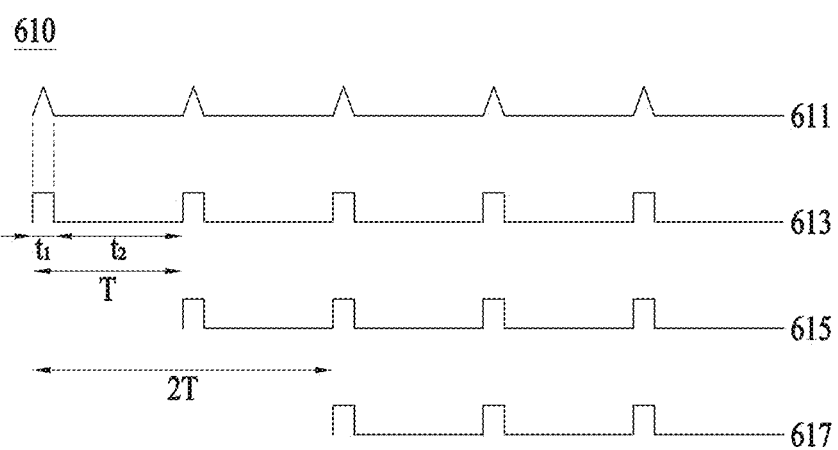
FIG. 6 is a diagram illustrating a driving signal according to an example embodiment.

FIG. 6 is a diagram illustrating a driving signal according to an example embodiment.

According to FIG. 610, the order of emission of visible light according to the pad may be confirmed. The above description is applicable here. The controller of the meridian stimulation device may transmit a driving signal to the light emitting unit to emit visible light in a specific order by applying the calculated delay time for each pad. Specifically, as shown in graph 611, the detection unit may detect a periodically repeated heartbeat. The controller of the meridian stimulation device may generate a driving signal to correspond 1:1 with the heartbeat cycle as shown in graph 613, and the light emitting unit may emit visible light during a heartbeat period t1 and may not emit visible light during a non-heartbeat period t2 according to the driving signal. The controller of the meridian stimulation device may generate a driving signal as shown in graph 615, and the light emitting unit may operate according to the driving signal with a period T delay compared to graph 613. Similarly, the controller of the meridian stimulation device may generate a driving signal as shown in graph 617, and the light emitting unit may operate according to the driving signal with a period 2T delayed compared to graph 613. That is, the controller may control to operate in the order of the pad corresponding to the graph 613, the pad corresponding to the graph 615 and the pad corresponding to the graph 617.

According to FIG. 620, the emission period of visible light according to the pad may be confirmed. The above description is applicable here. The controller of the meridian stimulation device may transmit a driving signal to the light emitting unit to emit visible light at a specific period by applying the period calculated for each pad. Specifically, as shown in graph 621, the detection unit may detect a periodically repeated heartbeat. The controller of the meridian stimulation device may generate a driving signal to correspond 1:1 to the heartbeat cycle as shown in graph 623. The controller of the meridian stimulation device may generate a driving signal to correspond 2:1 to a heartbeat cycle as shown in graph 625. Similarly, the controller of the meridian stimulation device may generate a driving signal to correspond 4:1 to the heartbeat cycle as shown in graph 627.

According to an example embodiment, since changes in the human body according to stimulation of acupuncture points may be different, the therapeutic effect may be improved through the order of the acupuncture points stimulated by changing the order of emission of visible light. In addition, by varying the emission period of visible light to vary the degree of stimulation of acupuncture points, the therapeutic effect may be improved.

Figure 7:
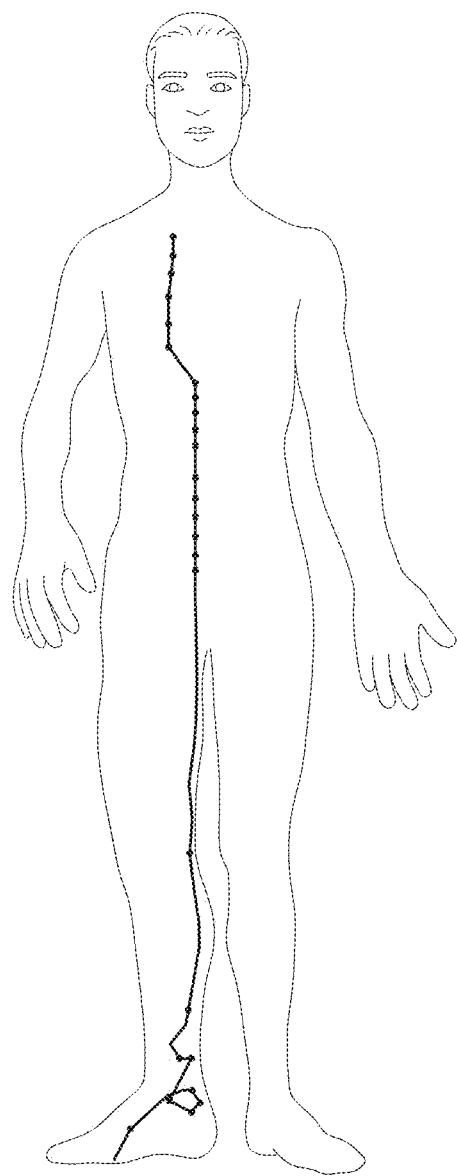
FIG. 7 is a diagram illustrating a Spleen Meridian on a classical meridian diagram according to an example embodiment.
Figure 8:
FIG. 8 is a diagram illustrating a change in the human body that appear when specific acupuncture points of a Spleen Meridian on a classical meridian diagram are stimulated with acupuncture needles according to an example embodiment.

FIG. 7 is a diagram illustrating a Spleen Meridian on a classical meridian diagram according to an example embodiment. FIG. 8 is a diagram illustrating a change in the human body that appear when specific acupuncture points of a Spleen Meridian on a classical meridian diagram are stimulated with acupuncture needles according to an example embodiment.

The ancients discovered meridians in the human body and left a classical meridian diagram as shown in FIG. 6, and thus treated many diseases based on acupuncture according to the classical meridian diagram. For example, many diseases were treated by changing the order of placing acupuncture needles on the acupuncture points on the classical meridian diagram or by changing the types of acupuncture needles (ex: long needles, short needles, and the like) according to the acupuncture points.

As shown in FIG. 7, the Spleen Meridian is a meridian related to menstrual irregularity, food poisoning, tuberculosis, gynecological disease, kidney, diabetes, asthma, pleurisy, and the like, and includes 21 acupuncture points. When a specific acupuncture point on the Spleen Meridian is stimulated with acupuncture needles, it can be confirmed through a thermal imaging camera that the temperature of the human body is sometimes increased as shown in FIG. 8. However, such an increase in the temperature of the human body does not appear to be a temperature increase according to the classical meridian diagram as shown in FIG. 7 and it is regarded as a special physiological phenomenon, but has not been used as an argument for the existence of meridians in the human body.

Figure 9:
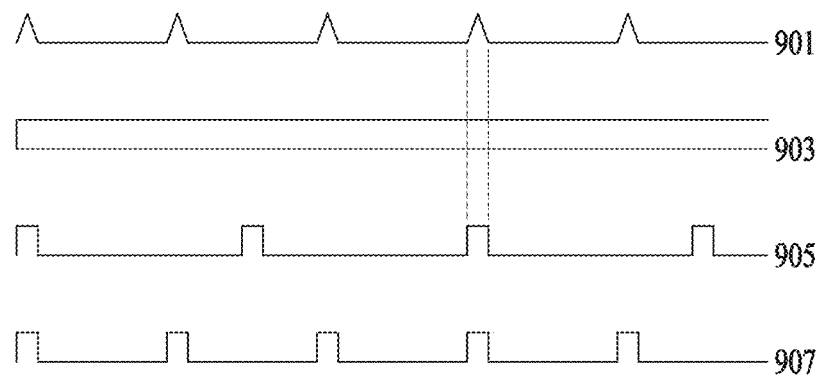
FIG. 9 is a diagram illustrating a driving signal corresponding to FIG. 10 to FIG. 12 according to an example embodiment.
Figure 10:
FIG. 10 is a diagram illustrating a change in a human body when visible light is continuously emitted according to an example embodiment.
Figure 11:
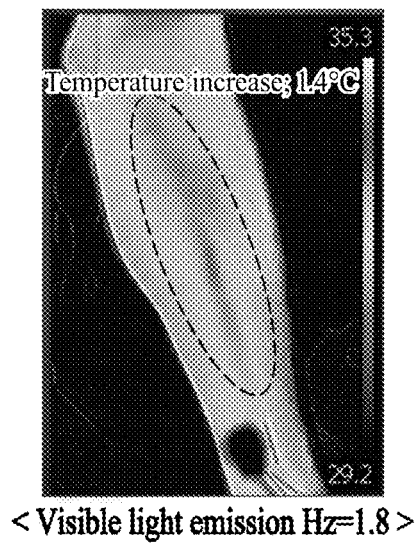
FIG. 11 is a diagram illustrating a change in a human body when visible light is emitted at 1.8 Hz according to an example embodiment.
Figure 12:
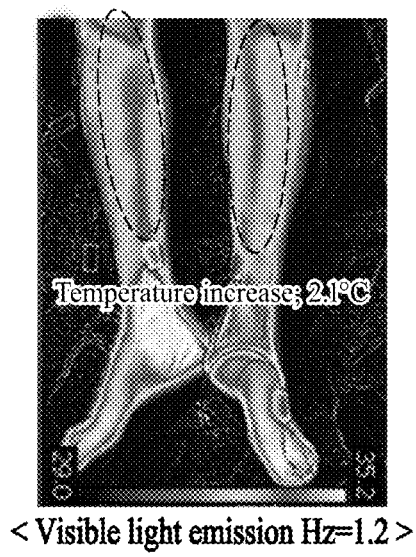
FIG. 12 is a diagram illustrating a change in a human body when visible light is emitted at 1.2 Hz according to an example embodiment.

FIG. 9 is a diagram illustrating a driving signal corresponding to FIG. 10 to FIG. 12 according to an example embodiment. FIG. 10 is a diagram illustrating a change in a human body when visible light is continuously emitted according to an example embodiment. FIG. 11 is a diagram illustrating a change in a human body when visible light is emitted at 1.8 Hz according to an example embodiment. FIG. 12 is a diagram illustrating a change in a human body when visible light is emitted at 1.2 Hz according to an example embodiment.

The detection unit of the meridian stimulation device may detect a heartbeat that is periodically repeated as shown in graph 901, and the controller of the meridian stimulation device may generate a driving signal and transmit it to the light emitting unit. The above description is applicable here. Here, it is assumed that the user's heartbeat cycle is 1.2 Hz.

When the controller of the meridian stimulation device transmits a driving signal to the light emitting unit to continuously emit visible light as shown in graph 903, resonance cannot occur due to visible light. Therefore, in the case of graph 903, the temperature increase along the Spleen Meridian on the classical meridian diagram as shown in FIG. 10 may not be confirmed.

When the controller of the meridian stimulation device transmits a driving signal to the light emitting unit so as to emit visible light at 1.8 Hz as shown in graph 905, the temperature may be partially increased along the Spleen Meridian on the classical meridian diagram as shown in FIG. 11 by the visible light. For example, when the controller transmits a driving signal to the light emitting unit to emit visible light at 1.8 Hz, as a result of taking a picture with a thermal imaging camera, it can be seen that the elevation of 1.4 degrees in some parts along the Spleen Meridian on the classical meridian diagram is confirmed as shown in FIG. 11.

When the controller of the meridian stimulation device transmits a driving signal to the light emitting unit to emit visible light at 1.2 Hz as shown in graph 907, the temperature may be increased along the Spleen Meridian on the classical meridian diagram by the visible light as shown in FIG. 12. For example, when the controller transmits a driving signal to the light emitting unit to emit visible light at 1.2 Hz in 1:1 correspondence with the heartbeat cycle, as a result of taking a picture with a thermal imaging camera, it can be seen that the elevation of 2.1 degrees along the Spleen Meridian on the classical meridian diagram was confirmed as shown in FIG. 12. That is, comparing FIG. 11 and FIG. 12, when visible light is emitted according to the heartbeat cycle, it can be confirmed that the temperature increases more clearly along the Spleen Meridian on the classical meridian diagram. Since there cannot be a physiological increase in the temperature in the blood vessels or lymphatic vessels of the human body, it can be seen that the temperature is increased as shown in FIG. 12 as energy flows along the meridians. That is, it can be seen that the temperature increases as shown in FIG. 12 as energy flows along the meridians by resonance generated by stimulating the acupuncture points by emitting visible light based on the heartbeat cycle. In this way, when the temperature increases part is connected, it may be confirmed that it is almost identical to the Spleen Meridian on the classical meridian diagram, and, because of this, it can be seen that the substance of the meridian has been objectively identified.

Meanwhile, in the present specification and drawings, a preferred embodiment of the present disclosure has been disclosed, and although specific terms are used, these are only used in a general sense to easily explain the technical content of the present disclosure and help the understanding of the disclosure, but it is not intended to limit the scope of the disclosure. It will be apparent to those of ordinary skill in the art to which the present disclosure pertains that other modifications based on the technical spirit of the present disclosure may be implemented in addition to the embodiments disclosed herein.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A meridian stimulation device, comprising:
a power supply unit configured to supply power;
a detection unit configured to detect a heartbeat cycle of the user while being attached to a skin of the user;
at least one pad comprising a light emitting unit that emits visible light and a filter through which the visible light is transmitted, the at least one pad configured to be attached to a predetermined position corresponding to a purpose of treatment for the user; and
a controller configured to control an operation of the light emitting unit so that the light emitting unit periodically emits the visible light based on synchronization with the heartbeat cycle of the user,
wherein the filter is formed by mixing iron (Fe), magnesium (Mg), calcium (Ca), lithium (Li), zinc (Zn), copper (Cu), molybdenum (Mo), chromium (Cr), nickel (Ni), nobelium (No), and selenium (Se) at predetermined ratios, and
wherein the controller is configured to control a wavelength of the visible light emitted from the pad to correspond to the purpose of treatment.

2. The meridian stimulation device of claim 1, wherein, in the filter, the iron (Fe), the magnesium (Mg), the calcium (Ca), the lithium (Li), the zinc (Zn), the copper (Cu), the molybdenum (Mo), the chromium (Cr), the nickel (Ni), and the nobelium (No), and the selenium (Se) are provided at different ratios to correspond to the predetermined position.

3. The meridian stimulation device of claim 1, wherein the predetermined position is a position corresponding to an acupuncture point of the user and is stimulated by the visible light passing through the filter.

4. The meridian stimulation device of claim 1, wherein the at least one pad comprises a filter including elements at different ratios to correspond to another predetermined position of the user.

5. The meridian stimulation device of claim 1, wherein the controller is configured to control an intensity of the emitted visible light based on the predetermined position of the user.

6. The meridian stimulation device of claim 1, further comprising:
a communication unit configured to receive learned data from an external server,
wherein the controller is configured to control the operation of the light emitting unit by reflecting the learned data.

* * * * *